(12) United States Patent
Lehmann

(10) Patent No.: US 7,005,294 B2
(45) Date of Patent: Feb. 28, 2006

(54) METHOD FOR PRODUCING AN ARRAY FOR DETECTING CONSTITUENTS FROM A BIOLOGICAL SAMPLE

(75) Inventor: Werner Lehmann, Lipten (DE)

(73) Assignee: Attomol Moleulare Diagnostika GmbH, Lipten (DE)

( * ) Notice: Subject to any disclaimer, the term of this patent is extended or adjusted under 35 U.S.C. 154(b) by 0 days.

(21) Appl. No.: 10/469,167

(22) PCT Filed: Feb. 27, 2002

(86) PCT No.: PCT/EP02/02116

§ 371 (c)(1),
(2), (4) Date: Mar. 15, 2004

(87) PCT Pub. No.: WO02/076608

PCT Pub. Date: Oct. 3, 2002

(65) Prior Publication Data

US 2004/0142338 A1    Jul. 22, 2004

(30) Foreign Application Priority Data

Feb. 28, 2001    (DE) ................................ 101 10 511

(51) Int. Cl.
  *C12M 1/34* (2006.01)
  *C12M 3/00* (2006.01)
(52) U.S. Cl. .................. 435/287.8; 83/915.5; 204/456; 204/464; 435/7.1; 435/287.7; 435/288.3; 436/524; 436/527
(58) Field of Classification Search ............... 83/915.5; 204/450–451, 456, 464; 427/2.11, 2.13; 435/6, 7.1, 287.7, 288.8, 805, 970, 287.8, 435/288.3; 436/516, 524, 527
See application file for complete search history.

(56) References Cited

U.S. PATENT DOCUMENTS

| 4,452,901 | A | * | 6/1984 | Gordon et al. ............. 435/7.92 |
| 4,820,504 | A | | 4/1989 | Battifora |
| 6,653,151 | B1 | * | 11/2003 | Anderson et al. ........... 436/518 |
| 6,713,309 | B1 | * | 3/2004 | Anderson et al. ........... 436/518 |

FOREIGN PATENT DOCUMENTS

| EP | 0238190 | 9/1987 |
| WO | WO 9617246 | 6/1996 |
| WO | WO 9913313 | 3/1999 |
| WO | WO 9919711 | 4/1999 |
| WO | WO 0040942 | 7/2000 |
| WO | WO 0205945 | 1/2002 |

OTHER PUBLICATIONS

Towbin, H. et al. (1979) Electrophoretic transfer of proteins from polyacrylamide gets to nitrocellulose sheets: Procedure and some applications. Proceedings of the National Academy of Sciences. vol. 76, No. 9, pp. 4350-4354.*

Elliott P. Dawson et al., "Membrane-based microarrays," Proceedings of the SPIE, SPIE, Sep. 1999, pp. 31-37, vol. 3857, XP000997211, the entire document, Bellingham, VA, US.

* cited by examiner

*Primary Examiner*—Long V. Le
*Assistant Examiner*—Leon Y. Lum
(74) *Attorney, Agent, or Firm*—Millen, White, Zelano & Branigan, P.C.

(57) ABSTRACT

The invention suggests a method of producing an array for the detection of components from a biological sample, wherein the detection molecules are immobilized on one or more supports, said support(s) is/are embedded and subjected to curing, the support is separated into sections, and the sections are applied on another support.

19 Claims, No Drawings

METHOD FOR PRODUCING AN ARRAY FOR DETECTING CONSTITUENTS FROM A BIOLOGICAL SAMPLE

The invention relates to a method of producing an array for the detection of components from a biological sample. The method is particularly suitable in the production of a compact array, because the detection molecules of the array can be coated on the array with very high density.

In clinical diagnostics and food analytics, immobilized detection molecules, e.g. enzymes and antibodies, have been used as recognition substances for various components in biological samples for several years. Where large numbers of such detection molecules are coated simultaneously on a single solid support, an array or microarray is concerned.

Using arrays, simultaneous investigation of a large number of samples is possible with low expenditure of material and work. For example, well-known arrays consist of a large number of microscopic spots, each of which may include identical detection molecules, e.g. single-stranded oligo-nucleotides, cDNA or antibodies, fixed on a solid support such as glass or a polymer. When fixing single-stranded oligonucleotides or cDNA, each spot will include a large number of copies of a particular sequence which may have 10–2000 bases.

In detection or analysis, there is an interaction with the sample, forming e.g. a double strand with a complementary sequence—the so-called hybridization. If the spots of the detection molecules include e.g. copies of particular antibodies, analysis or detection proceeds via interaction with antigens of a biological sample, thereby forming antigen-antibody complexes.

When using arrays, the density of coated and immobilized detection molecules, e.g. DNAs, antibodies and/or receptors, is highly important.

Medium-density arrays have 100 to 1000 different immobilized detection molecules, and the so-called high-density arrays have about 10,000 immobilized molecules. Particularly in the production of the so-called high-density chips or arrays, there are some drawbacks with respect to the capability of mass production. For example, these drawbacks involve the complex immobilization procedure and the costly production process. Another drawback in the previous methods of producing arrays or microarrays is that the arrays, particularly for clinical uses, cannot be produced with the required reproducibility. That is, arrays for routine investigations coated e.g. with the same antibodies or receptors vary in their structure and in the density of coated immobilized molecules, rendering comparisons between the investigations difficult or impossible.

Various ways of achieving the above objective have been followed. Thus, WO/09607 A1 describes an arrangement of fibrillar supports embedded in an embedding medium so as to allow production of thin sections perpendicular to the longitudinal axis of the fibrils, which sections have identical cut surfaces of all fibrils and may serve as array. However, arranging a large number of fibrils is complex in practice and in addition, the materials of the fibrils might adversely affect the subsequent analysis of biomolecules. The analysis of complex protein mixtures is difficult to accomplish. To allow imaging of complex distribution patterns of biomolecules in biological tissues, a tissue array has been patented (U.S. Pat. No. 4,914,022). Therein, samples of selected tissues are embedded together in a paraffin block, dissected, and the sections are placed on a support. While the above invention enables investigations of the distribution patterns in various tissue sections, classification on a molecular level as e.g. in a Western blot following 1D or 2D separation of protein mixtures is not possible.

The invention therefore is based on the object of providing a method of producing an array for the detection of components from a biological sample, which method allows for low-cost and simple production of arrays with good reproducibility even with highly complex samples.

The present invention solves this technical problem by providing a method of producing an array for the detection of components from a biological sample, wherein the detection molecules are immobilized on a first support, at least one first support is embedded in a material, said material is subjected to curing, the embedded first support is separated vertically into sections, at least one section is applied on a second support such that the detection molecules make contact with the second support, and the cured material and/or the first support are completely or partially dissolved or removed from the applied section using a solvent, and the array is obtained.

In the meaning of the invention, arrays can be specific membrane components enabling, facilitating or accelerating permeation of material through biomembranes. In the meaning of the invention, however, arrays also are insoluble organic and inorganic, macromolecular materials such as porous glass, PVDF membranes and the like, to which soluble components such as enzymes and even microorganisms can be bound so as to allow detection of substances via these components.

In the meaning of the invention, a biological sample is any material obtained from microorganisms, plants, animals, or humans. Biological samples in the meaning of the invention therefore comprise blood, serum, chromosomes, fetuses, tissue samples, gametes, urine, feces, lacrimal fluid, secretions, respiratory air, perspiration, mucous smears, bone material, cartilage, hair, proteins, nucleotide sequences, carbohydrates, lymph, intestinal contents, degenerate tissue, cells, cell fragments, DNA, RNA, lipids, and the like. Biological samples in the meaning of the invention can also be subquantities collected from waste waters, residues from industrial processes, bogs, or from other environmental fluids. Hence, a sample in the meaning of the invention is any material collected by sampling, or a portion or small amount thereof, the nature of which is to be investigated by physical, chemical and/or biological means.

According to the invention, detection molecules are all those substances allowing determination or detection of components from a biological sample. Where antigenic structures are to be investigated in a biological sample, the detection molecules in the meaning of the invention are antibodies, for example. However, detection molecules can also be receptors interacting with signal molecules in the biological sample. Moreover, detection molecules can also be DNA or RNA sections hybridizing with DNA and RNA sections in the biological sample. In the meaning of the invention, detection molecules can also be microorganisms, cells or cell extracts.

A support in the meaning of the invention is a material to which soluble detection molecules can be bound.

In the meaning of the invention, immobilization is understood to comprise all those methods resulting in a restriction of the mobility and solubility of detection molecules by chemical, biological and/or physical means. Immobilization can be accomplished using various methods, such as binding of detection molecules to each other or to a support, entrapping in the network of a polymer matrix, or enclosing by membranes. As a result of immobilization, the detection molecules not only are made reusable, but also, they can easily be removed subsequent to the process of interaction with the biological sample. They can be used at much higher local concentrations and in continuous flow systems. The detection molecules can be bound to or immobilized on the support by direct support binding and by crosslinking. According to the invention, support binding or crosslinking particularly proceeds via ions/adsorption or via covalent binding. Crosslinking in the meaning of the invention is crosslinking of detection molecules with each other or with other polymers. Immobilization by inclusion involves inclusion of the detection molecules in gel structures or in membranes.

According to the inventive method of producing an array, the detection molecules are immobilized on a planar or non-planar first support. The first support can be a membrane, e.g. a nitrocellulose membrane. Detection molecules can be immobilized on the first support e.g. by dripping round spots or imprinting lines thereon.

As first supports, it is possible to use both planar and non-planar bodies such as spheres, cuboids, or fibrils and bars which are impregnated with various detection molecules and subsequently transferred into an embeddable and dissectable spatial arrangement.

Numerous ways of immobilizing the detection molecules on the first support are known to those skilled in the art. Immobilization is to be effected in such a way that each probe can be related to a defined position on the support, and that each position on the first support can be evaluated independently. However, it may also be desired to have partial or complete overlap of the application points of different probes or to apply mixtures of probes. For example, immobilization can be effected using a method derived from semiconductor technology. Essentially, the detection molecules can be immobilized on the first support in two principally different ways: firstly, an in situ synthesis of the detection molecules at well-defined positions on the first support by successive coupling of monomeric components of synthesis is possible; secondly, detection molecules previously synthesized or derived from libraries can be placed and immobilized on well-defined positions of the particularly functionalized support material. To this end, both spotting and printing procedures can be used. Spotting is understood to comprise procedures wherein liquid drops containing the detection molecules are placed on the support, forming essentially round spots as a result of surface interactions and drying. However, other printing procedures also enable application of detection molecules in well-defined areas on the surface of the first support, allowing for stable binding of samples to the substrate surface of the detection molecules with high coupling efficiency. Similarly, any measure known to those skilled in the art for immobilizing biomolecules on e.g. column materials can be used to immobilize the detection molecules on the first support.

For example, selected immobilization procedures are contact tip printing, ring-and-pin printing, nanoelectric printing and nanopipetting, bubble jet printing, top spot printing, microcontact printing, micro-fluidic networks methods, photolithographic activation method, photoresist lithography, electrochemical focusing and micro-wet printing. However, comparatively simple sample applicators from thin layer chromatography or HPLC autosamplers can also be used.

Using the above procedures, it is possible to obtain a spot size ranging from less than one micrometer to more than 1000 micrometers. According to the invention, the probe density per $cm^2$ may range from about 1 to 1 million, for example. The above-mentioned procedures permit easy handling and high precision of volumes applied, as well as highly homogeneous spots which can be applied in a highly paralleled fashion. In particular, the procedures allowing for direct synthesis of detection molecules on the first support involve high integration density and a simple combination of immobilization and hybridization. The detection molecules, also referred to as probes, can also be prepared by means of additional procedures in order to keep the amount of non-specifically synthesized or bound detection molecules low.

However, the detection molecules can also be immobilized on the first support using a blot procedure. To this end, detection molecules such as antibodies, receptors, tissue extracts, microorganisms and the like are separated by means of electrophoresis. The electrophoretic separation can be effected using one-dimensional or multi-dimensional electrophoresis, particularly 2D electrophoresis.

The detection molecules separated by electrophoresis are subsequently transferred either onto the first support or onto a membrane which is placed on the first support in a following step.

According to the invention, at least one first support having the detection molecules immobilized thereon is embedded in a material. A variety of biological and chemical embedding materials are known to those skilled in the art. The material should be chemically inert to the largest possible extent, so as to prevent interaction thereof with detection molecules in a way that would adversely modify the latter.

However, modification of the detection molecules by interaction with the material can also be envisaged. Obviously, it is also possible to do without embedding in those cases where the first support(s) is/are of a dissectable consistency. That is, if the consistency of the support(s) allows dissection without any treatment, the support(s) does/do not require embedding.

For example, the material may consist of saturated hydrocarbons and can be present in solid state at room temperature. Furthermore, the material can be of a nature which allows liquefaction by means of conventional laboratory methods, e.g. by heating or ultrasonic treatment. Regarding the support to be embedded, with the immobilized detection molecules thereon, the material should retain its liquid state even at temperatures below 60° C. Above this temperature, some proteins and peptides or extracts of tissues and/or microorganisms begin to undergo denaturation.

In another process step of the method according to the invention, the material is made to cure. For example, curing can be effected by simple cooling of the material or by addition of chemical substances which initiate curing of the material. However, it is also possible to cure the material by physical exposure such as ultrasound or UV radiation or X-rays. Curing of the material should proceed in such a way that adverse modification of the first support and of the detection molecules is avoided. Curing of the material stabilizes the support in its embedded position, thereby allowing e.g. mechanical, chemical or biological treatment thereof.

In a further step of the method according to the invention, the embedded first support(s) is/are separated into vertical sections. If, owing to their consistency, the first supports can be separated into sections without any treatment, e.g. by embedding, separation of course is effected on non-embedded supports. Where the detection molecules are immobilized on the support in the form of multiple lines, the sections can be separated so as to form sections having multiple spots of immobilized detection molecules thereon, which represent portions of the separated lines. Obviously, the individual spots on the section are spaced apart by the same distance as the lines on the first support.

In a further step of the method according to the invention, at least one section is placed on a second support, so that the detection molecules make contact with the second support. For example, application of multiple sections, e.g. side by side, on the second support can be envisaged. Sections separated from one and the same first support may have a virtually identical structure of coated detection molecules. In particular, when applying several of these similar sections on one and the same second support, efficient clinical routine and screening investigations with appropriate options of comparison and control are possible. One particularly advantageous option of use is differential-diagnostic investigations.

The section or sections are applied on the second support in such way that the detection molecules are linked with the second support or contact the second support. Applying the section on the second support can be effected by simple lay-up, where adhesion and cohesion forces may have a beneficial influence in fixing the section on the second support. For example, this can be achieved by placing the section on a drop of liquid and heating to stretch the section. However, the use of special substances or devices well-known to those skilled in the art can also be envisaged in order to apply one or more sections on the second support and fix them in a desired position. For example, the second support can be a glass slide held in horizontal position, so that one or more sections can be placed thereon. However, the sections can also be placed on the bottom of a microtest plate or on a membrane, for example.

According to the method of the invention, the cured material and/or the first support are completely or partially removed from the sections, thereby obtaining the array. As a result of complete or partial removal of first support and/or cured material, the detection molecules in particular are bound to the second support. For complete or partial removal of cured material or first support, various solvents are known to those skilled in the art. The nature of the solvent should be such that the detection molecules are retained in their three-dimensional structure and functionality to the largest possible extent. More specifically, the solvent can be selected so as to allow stabilization of the detection molecules and, if required, preservation with highest possible activity under most various conditions of stress even for months. As a result of dissolving the first support and/or the material, the detection molecules are fixed on the second support, so that repeated use under technical conditions is possible. The detection molecules can be bound by the second support via adsorption, ionic binding or covalent binding. In those cases where the detection molecules are enzymes, proteins, nucleic acids, carbohydrates, lipids, etc., this may also take place inside the original microbial, vegetable or animal cell, or in a virus. Binding of the detection molecules to the second support allows multiple and continuous use thereof.

Binding to the support may also proceed via inclusion, as in cases where e.g. the second support is a semipermeable membrane in the form of gels, microparticles or fibers. Now, the detection molecules thus enclosed are separated from the surrounding biological sample by a semipermeable membrane. In particular, spatial fixing by inclusion has no influence on the activity of the detection molecules. For example, inclusion of detection molecules is also possible in those cases where the second supports are sintered glass frits or blotting membranes, thereby allowing concentrating of the detection molecules. For example, such concentrating can be effected by means of capillary blotting using a liquid flow or by electroblotting. Concentrating or transfer of the detection molecules can also be effected by dissolving the first support on the second support. Preferably, such dissolving can be effected in such a way that the solvent preferably soaks into the second and first supports from below in a semi-dry process. However, the solvent can also be applied as an aerosol from above, so that first and second supports will be soaked from above.

Furthermore, immobilization on the second support is possible by gel inclusion in carragheen, in alginate, or in ENT polymers, by inclusion in polyacrylamide, or on ceramics and on ceramic supports with polyamine, and/or by means of crosslinking using glutaraldehyde.

Furthermore, the second support can be designed as an ultrafiltration membrane having entrapped detection molecules positioned downstream or upstream thereof.

Macroporous supports are preferred in those cases where a largest possible surface for adsorption or covalent binding is to be achieved. One possible precondition for covalent fixing of detection molecules is the presence of functional groups on the support. One possible activation procedure, e.g. with dextran gels, is reaction with bromocyanogen. According to the chemical nature of the functional groups, various types of binding can be formed, e.g. ethers, thioethers, esters, etc. Furthermore, coupling procedures for covalent linkage of detection molecules to agar, agarose and Sephadex supports, and to silanized surfaces of porous glasses are well-known to those skilled in the art. Possible changes in the activity of the detection molecules can be avoided or reduced by immobilizing the detection molecules via spacers to the second support, the option of treating first and second supports identically or differently being known to those skilled in the art. More specifically, the spacers confer higher mobility to the detection molecules, allowing unimpeded contact with the biological sample. Optional crosslinking of detection molecules by bi- or multifunctional spacer molecules allows immobilization of greater amounts of detection molecules on the second support. For example, the spacers can be added to the solvent used for complete or partial removal of cured material and/or first support. Obviously, spacers can also be used to immobilize the detection molecules on the first support.

When separating the detection molecules by means of a 2D electrophoresis, the separated sections may include such spots or not, depending on the position of the individual spots which, in particular, are point-like in shape. For example, if a spot has a diameter of one millimeter, and sections are separated in a range of one tenth of a millimeter, about 10 sections would include this spot. If each second support is to include all the spots of the first support, the corresponding sections, after completed dissection of the first spot and beginning dissection of the next following spot, are immobilized on the second support which already has the sections of the preceding spot. Obviously, it might also be envisaged that the second supports do not have all the spots of the first support, but merely comprise a few spots of the first support.

In a preferred embodiment of the invention, at least two first supports are embedded in overlap in the material. Such overlapping of at least two first supports advantageously allows production of highly compact arrays. For example, two or more first supports including detection molecules arranged in line-shape can be positioned one on top of the other. The density of the detection molecules firstly depends on the spacing of the lines on each first support and secondly on the packing density of the embedded first supports with respect to each other. When selecting very thin first supports, e.g. membranes, high-density packing of multiple membranes one on top of the other is possible. Advantageously, the first supports can be selected in such a way that a highest possible number of detection molecules can be arranged on the surface, e.g. by means of a printer. Conveniently, stability requirements to be met by any array are less important because the support actually used is the second support. More specifically, the second support can be selected according to stability criteria or other criteria significant e.g. in clinical routine operation.

For example, 50, 100 or more first supports, e.g. membranes very thin in shape, can be placed one on top of the other and embedded in the material. By dense line-shaped or point-like application of a large number of detection molecules and by using a large number of first supports arranged in overlap one on top of the other, it is possible to achieve a very high density of detection molecules. Thereafter, the first supports arranged in overlap are dissected vertically, e.g. in a perpendicular to the line of coated detection molecules. The section now includes the detection molecules of the mutually arranged supports, as well as a few spots of detection molecules arranged on one support at a time, thereby allowing formation of highly compact arrays.

In another advantageous embodiment of the invention, microorganisms, cells, cell extracts, ligands, antigens, antibodies, receptors, nucleic acids, lectins, proteins, peptides, glycopeptides, carbohydrates, and/or lipids are employed as detection molecules. The microorganisms can be living or dead microorganisms, and living microorganisms in the meaning of the invention may concern both growing and resting cells. For example, microorganisms can be immobilized on the first support by adhesion and growth. Passive immobilization resulting in microbial growth will form a biofilm on the first support. Apart from van-der-Waals forces, other binding forces such as hydrophobic interactions, hydrogen bridges, and ionic binding contribute to the development of adhesion. The adhesiveness depends on the chemical composition, overall charge and age of the microorganisms, and on the charge, composition, and also, on the porosity of the first support. More specifically, glass, titanium dioxide and zirconium dioxide, cellulose, nitrocellulose, nylon, and polyvinyl alcohol membranes can be used as first supports for microorganisms. The microorganisms can also be immobilized on the first support by intracellular and intercellular crosslinking of cells. Conveniently, biopolymers such as polysaccharides or proteins and also, synthetic polymers, particularly polyacrylamide, are used for inclusion in a polymer matrix to immobilize the microorganisms, forming e.g. biopolymer beads. These biopolymer beads having the cells enclosed therein are fixed either by chelating or by crosslinking, using e.g. glutardialdehyde. In the inclusion procedures used to immobilize microorganisms, the pores of the first support advantageously are smaller than the microorganisms. Consequently, the microorganisms will remain in the inclusion, while substrates and products from the biological sample can flow in and out. However, the microorganisms can also be immobilized on the first support by encapsulation in membranes. In the meaning of the invention, it is possible to distinguish between encapsulation in solid and in liquid membranes. For example, solid membranes are formed from prefabricated membranes, e.g. in membrane reactors such as hollow fiber membrane reactors, or the membrane is formed immediately around the cell suspension, as is the case in microencapsulation, for example. Liquid membranes are formed by the phase boundary between two non-miscible liquids, for example. Advantageously, immobilization has only a small effect on the functionality or physiological condition of the microorganisms. For example, immobilized microorganisms offer the advantage of easier cell removal and cell retention. Another advantage is that enzymes in the microorganisms, being in their natural micro-medium, conveniently have higher resistance to pH and temperature and higher stability in operation. Advantageously, multi-enzyme reactions are therefore easier to perform compared to immobilized enzymes. In particular, this also applies to coenzyme-dependent reactions with in situ regeneration of coenzymes/cofactors.

The use of immobilized microorganisms is particularly advantageous in those cases where (i) the enzymes involved in the conversion of materials are located inside the cell, (ii) the enzymes isolated from the cells are unstable during and subsequent to immobilization, (iii) the microorganisms do not contain any interfering enzymes, and/or (iv) the enzymes can easily be inactivated or removed, and (v) the substrates and products have low molecular weights. Obviously, the microorganisms can also be immobilized together with enzymes on the first support. Coimmobilization in the meaning of the invention is immobilization of intact, living or dead cells of microorganisms together with free or immobilized enzymes; for example, immobilized enzymes, together with whole cells, can be entrapped in a common matrix, or the enzymes can be directly coupled to living cells which are subsequently immobilized on the first support. Advantageously, a high percentage of the microorganisms retain their viability. As a result of coimmobilization of microorganisms and appropriate enzymes, it is possible, among other things, to render substrates fermentable which otherwise could not be fermented by the organism, and the products thus formed can interact with the detection molecules or with the biological sample. In total, coimmobilization can contribute in expanding the spectrum of use of the array. Furthermore, cell extracts and cell compartments can be immobilized as detection molecules on the first support. Within a cell, numerous types of molecules are confined to specific areas, i.e., the compartments. In the cell, this is achieved by separation by membranes impermeable to particular substances. In addition, by having compartments in cells or cell extracts, separate reaction volumes are created wherein free diffusion is blocked to a large extent, because the molecules or enzymes are bound to well-defined structures. Advantageously, application of cell extracts or cell compartments will also immobilize the separate reaction volumes on the first support.

Obviously, it is also possible to use ligands as detection molecules. For example, ligands in the meaning of the invention are molecules such as proteins or ions which can be arranged around a central structure. Ligands can be monodentate and polydentate. However, ligands can also be regarded as molecules that are bound to specific sites of macromolecules, e.g. substrates or coenzymes to a protein.

Antigens and/or antibodies can also be used as detection molecules with advantage. Antigens in the meaning of the invention are all those substances capable of inducing an immune response. These can be exogenic, natural or synthetic macromolecules, especially proteins and polysaccharides, with a molecular weight of more than 2 kD, as well as surface structures of foreign particles. An antigen according to the invention may comprise a high-molecular weight portion serving as substrate for—mostly several—low-molecular weight groups, e.g. haptens, which are crucial to the specificity of the immune response and to the reaction of antigens with the corresponding immunoglobulins. The antigens can be polyvalent and monovalent, thus being capable of interacting with one or more types of antibodies.

However, immobilization of antibodies instead of antigens on the first support can also be envisaged. More specifically, antibodies are understood to be glycoproteins interacting specifically with an antigen. This interaction results in the formation of antigen-antibody complexes. For example, the antibodies can be various groups of immunoglobulins. Obviously, the antibodies can be immobilized in the form of intact antibodies or in the form of various fragments which can be obtained e.g. by cleavage using various peptidases. The antibodies can be modified prior to, during or subsequent to immobilization on the first support, e.g. by reduction, oxidation, or by oligomerization.

Receptors can also be used as detection molecules with advantage. For example, receptors are proteins interacting with extracellular signal molecules, e.g. with a ligand, activating or initiating specific functions via conformational changes, particularly via secondary messenger substances. However, receptors in the meaning of the invention can also be specific cells which receive stimuli and pass on the corresponding information; examples are photo-, chemo-, thermo- and baroreceptors.

Furthermore, lectins can also be immobilized as detection molecules on the first support. For example, lectins according to the invention are sugar-binding proteins or glycoproteins of non-immune origin, which agglutinate cells and/or precipitate glycoconjugates. However, proteins may also be concerned, which specifically bind complex saccharides, but do not agglutinate or precipitate the latter. For example, such proteins are monovalent lectins. The lectins can be recovered from plants, invertebrates, vertebrates and/or microorganisms. They can be used as detection molecules to bind e.g. erythrocytes, leukemia cells, yeasts, and some types of bacteria. Advantageously, binding of lectins with substances from a biological sample is saccharide-specific. For this reason, immobilized lectins advantageously do not agglutinate those cells lacking the appropriate surface saccharides; that is, such cells could be excluded by an infectious agent or by non-binding. Examples of lectins to be used are concanavalin A from jack beans, agglutinins from wheat germs, lima beans, garden beans, soy beans, castor beans, and potatoes. More specifically, it is possible to detect various types of protein maturing when using concanavalin A.

So-called aptamers can also be used as detection molecules. In particular, they are understood to be peptides, DNA or RNA molecules which, owing to their specific molecular shape and charge, are capable of binding other molecules in a specific fashion.

According to another advantageous embodiment of the invention, the detection molecules are immobilized on the support in the form of multiple lines. For example, the first support can be a gel which is used to separate an extract or a mixture of detection molecules. Depending on the type of application on the gel, separate bands or continuous lines would form, according to the isoelectric point, molecular weight or the like. However, the detection molecules in the gel can also be blotted on a membrane which then acts as first support. Other methods of immobilizing the detection molecules in multiple lines on a support will be familiar to those skilled in the art. For example, possible procedures are contact tip printing, ring-and-pin printing, photoresist lithography, and micro-wet printing.

In another advantageous embodiment of the invention, it is envisaged to transfer the detection molecules from a gel onto the first support by means of Western and/or Southern blotting.

In another advantageous embodiment of the invention, the use of supports comprising nitrocellulose, polyvinylidene difluoride (PVDF), cellulose acetate, cellulose mixed esters, polytetrafluoroethylene (PTFE), polyamide, regenerated cellulose, polycarbonate, polyester, polysulfone, polyacrylamide, agarose, nylon, and/or polyprene as first support is envisaged. In particular, the first support can be selected such that immobilization of a very large number of detection molecules is possible, because it is the second support that is actually used as support. Advantageously, the first support especially may comprise nitrocellulose. Nitrocelluloses in the meaning of the invention are inorganic cellulose esters. Furthermore, it is possible to use nylon as first support, with nylon in the meaning of the invention comprising linear aliphatic polyamides which, in particular, have a high melting point. It is also convenient to use polyvinylidene fluorides as first support. Polyvinylidene fluorides are thermoplastics which are easy to process and advantageously, have a high resistance when exposed to temperature and chemicals. Obviously, it is possible to use polyvinylidene fluorides having varying degrees of crystallinity which can be achieved by rapid or slow cooling, particularly during production. Advantageously, polyvinylidene fluorides are remarkable for their high mechanical strength, rigidity and tenacity even at low temperatures. Conveniently, the first support may also comprise cellulose acetate, with cellulose acetate in the meaning of the invention being cellulose esters produced by reaction of linters or cellulose with acetic anhydride in acetic acid or methylene chloride as solvent, using strong acids as catalyst in a batch process. Advantageously, cellulose acetates are remarkable for their high strength, impact strength, scratch resistance, translucency, and surface gloss, and they can easily be surface-finished by imprinting, varnishing, hot embossing or metallizing. Advantageously, the first support may also comprise cellulose esters or other cellulose derivatives. In the meaning of the invention, cellulose derivatives are substances formed by polymer-analogous reactions of chemically modified cellulose. Included are products wherein hydroxy hydrogen atoms in the anhydroglucose units of the cellulose are substituted by organic or inorganic groups solely by esterification and/or etherification reactions, as well as products formed by formal replacement of hydroxy groups in the natural polymer by functional groups not bound via an oxygen atom, or formed via intramolecular elimination of water or by oxidation reactions. In the meaning of the invention, cellulose esters are cellulose derivatives which can be produced by esterification of linters or cellulose with organic and/or inorganic acids or acid derivatives which also can be used as mixtures. Especially cellulose mixed esters may have good water insolubility and/or thermoplastic properties. Obviously, the first support may also comprise other plastic materials and/or polymers. Plastic materials in the meaning of the invention include modified natural materials, thermoset materials and thermoplastics, as well as synthetic plastics, e.g. polycondensates, polymers and polyadducts. Examples of such compounds are: acrylonitrile-butadiene-styrene, acrylonitrile-methyl methacrylate, cellulose acetobutyrate, cresol-formaldehyde, carboxymethyl-cellulose, casein, diallyl phthalate, ethylcellulose, epoxide, expandable polystyrene, ethylene-vinyl acetate, ethylene-vinyl alcohol, tetrafluoroethylene-hexafluoropropylene, high-density polyethylene (rigid PE), low-density polyethylene (plasticized PE), methyl methacrylate-butadiene-styrene, methylcellulose, melamine-formaldehyde, polyamide, polymer of ε-caprolactam, polycondensate of hexamethyl-enediamine and adipic acid, polyacrylonitrile, polybutene, polybutylene terephthalate, polycarbonate, polychloro-trifluoroethylene, polyethylene, chlorinated polyethylene, ethylene-propylene, polyethylene terephthalate, phenol-formaldehyde, polyimide, polyisobutylene, polymethyl methacrylate, polyoxymethylene, polyacetal, polypropylene, polyphenylene oxide, polyphenylene sulfide, polystyrene, polytetrafluoroethylene, polyurethane, polyvinyl acetate, polyvinyl alcohol, polyvinyl chloride, polyvinylcarbazole, polyvinylpyrrolidone, styrene-acrylonitrile, polystyrene modified with elastomer based on butadiene, silicone, styrene-α-methylstyrene, urea-formaldehyde, and/or unsaturated polyesters.

Advantageously, such plastic materials have low specific weight, high resistance to corrosion and high electric insulating capacity, easy molding, and good printability, especially for detection molecules. Polymers in the meaning of the invention are products formed by polyreactions, e.g. by polymerization, polyaddition and/or polycondensation, or by polymer-analogous reactions. Monomers resulting in polymer compounds can be e.g. ethylene, styrene, vinyl chloride, vinyl acetate, methyl methacrylate, and/or ethylene oxide.

In another advantageous embodiment of the invention, the use of saturated aliphatic hydrocarbons, especially paraffin, embedding resins, collagen solutions, aqueous solutions, solutions of crosslinking proteins, carbohydrates, nucleic acids, polymers, and/or agarose as curing material is envisaged. Hydrocarbons in the meaning of the invention are organic compounds comprising carbon and hydrogen. Obviously, the hydrocarbons may also comprise further substances or compounds such as oxygen, nitrogen, sulfur, phosphorus, or specific functional groups. Paraffins in the meaning of the invention represent a solid or liquid mixture of especially saturated aliphatic hydrocarbons, which advantageously is colorless, odorless and tasteless, readily soluble in xylene, ether and chloroform, insoluble in water and 70% alcohol, and does not exhibit fluorescence. Collagen solutions in the meaning of the invention comprise collagen. Collagens are long-fiber, linear-colloidal, high-molecular weight scleroproteins particularly occurring in the extracellular matrix, in connective tissue, in the proteinaceous background matrix of bones, and in dentin. In the meaning of the invention, agarose comprises gel-forming polysaccharides from agar, especially consisting of alternating moieties of β-1,3-linked D-galactopyranose and α-1,4-linked 3,6-anhydro-L-galactopyranose, wherein the galactose can be methylated in the 6-position. Aqueous solutions are solutions which comprise water and, in particular, undergo curing at low temperatures.

In another advantageous embodiment of the invention, the use of supports comprising a metal, polypropylene, teflon, polyethylene, polyester, polystyrene, ceramics, and/or glass as second support is envisaged. Metals in the meaning of the invention are all those materials wherein cohesion is furnished by a crystal lattice. The dividing-line between metals and non-metals is blurred, so that the elements Ce, Sn, As, and Sb are also metals in the meaning of the invention. Metals according to the invention also include metallic glasses, i.e., materials being in a metastable, largely amorphous state. Obviously, polymers having metallic conductivity are also included in the meaning of the invention. Advantageously, metals in the meaning of the invention have good strength, good hardness and wear resistance, high tenacity, and good electric and thermal conductivity. Polypropylenes in the meaning of the invention are thermoplastic polymers of propylene. Polypropylenes are remarkable particularly for their high hardness, resilience, rigidity, and heat resistance. However, the second support may also comprise teflon. Teflon in the meaning of the invention is a polytetrafluoroethylene which advantageously has good thermoplastic properties. More specifically, polyethylenes are formed by polymerization of ethylene according to essentially two different methods, i.e., the high-pressure and low-pressure processes. Polyethylenes produced in the high-pressure process advantageously have low density. Essentially, the properties of the second supports comprising polypropylene are determined by the character of the polyethylene as a partially crystalline hydrocarbon. Advantageously, polyethylenes are virtually insoluble in all common solvents up to 60° C. Advantageously, polar liquids such as alcohols, esters and ketones barely cause swelling of polyethylenes at room temperature. Advantageously, polyethylenes are completely inert when exposed to water, alkaline solutions, salt solutions and inorganic acids. For example, supports comprising polyethylenes have a very low water vapor permeability. Conveniently, the second support may also comprise polyesters. Polyesters in the meaning of the invention are compounds produced by ring-opening polymerization of lactones or by polycondensation of hydroxycarboxylic acids or of diols and dicarboxylic acids or dicarboxylic acid derivatives. Polyesters in the meaning of the invention also comprise polyester resins, polyester imides, polyester rubbers, polyesterpolyols, and polyesterpolyurethanes. Advantageously, polyesters are thermoplastics and have distinct material character. They are remarkable for their high thermal stability and can be processed into alloys with metals such as copper, aluminum and magnesium. However, It can also be envisaged that the second support comprises ceramics. Ceramics in the meaning of the invention is a collective term for an especially inorganic class of materials predominantly consisting of non-metallic compounds and elements and particularly comprising more than 30% by volume of crystalline materials. Various ceramics or ceramic materials which can be used as second support will be familiar to those skilled in the art. For example, pottery, earthenware crockery, split wall tiles, laboratory porcelain, crockery porcelain, bone china, aluminum oxide ceramics, permanent magnet materials, silica bricks, and magnesia bricks can be concerned. In the meaning of the invention, clay-ceramic materials are classified in coarse and fine materials, with fine clay-ceramic materials comprising earthenware, stoneware and porcelain. Advantageously, specialty ceramics such as glass and oxide ceramics, SiC bricks, and melt-cast bricks can also be used as second supports. Preferably, the second support may also comprise glass. Glass in the meaning of the invention comprises materials in amorphous, non-crystalline solid state, i.e., the glassy state in the meaning of the invention can be regarded as frozen, subcooled liquid or melt. Thus, glass materials are inorganic or organic, mostly oxide melted products converted into a solid state by an introduction process without crystallization of the melt phase components. Obviously, crystals, melts, and subcooled melts are also to be regarded as glass materials in the meaning of the invention. For example, glass materials can be flat glass, container glass, commercial glass, laboratory glass, lead glass, fiber glass, optical fiber glass, and others. obviously, it is also possible to use glass materials free of silicate, e.g. phosphate glass materials. However, the nature of the second support can be such that optical glass, i.e., glass material having a specific optical refractory index is used.

In another advantageous embodiment of the invention, modification of the support surface is envisaged. More specifically, modification of the supports can be effected by biological, physical and/or chemical exposure. For example, physical exposure would be polishing, etching, pickling, sandblasting, also including physical procedures resulting in curing, coating, finishing, coating with a protective skin, and the like. For example, surface treatment by biological exposure may include colonization by microorganisms. Chemical modification of the support surface may involve e.g. treatment with acids, bases, metal oxides and others. The surface of the supports can be modified in such a way that the detection molecules have particularly good adherence on the support, or adherence that would not adversely modify the activity thereof. Surface modification also comprises coating with poly-L-lysines, aminosilanes, aldehydesilanes, epoxy groups, gold, streptavidin, branched linkers, reactive groups, polyacrylamide pads, immobilized nitrocellulose, and/or activated aldehydes or agarosealdehyde groups, particularly binding: DNA, $COO^-$ groups, $NH_2$ groups, biotin, thiol groups and others. Of course, surface modification of the supports also comprises a treatment resulting in increased stability and breaking strength especially of the second support. Obviously, traditional surface modification as used in histology, such as coating of first or second supports with e.g. proteoglycerol, polylysine, activated dextrans, or bichromated gelatin, can also be performed. Likewise, melt-coating or surface drying of the first support on the second support is possible. Surface drying is a process which preferably can proceed between 20 and 100° C., and between 37° C. and 80° C. in a particularly preferred embodiment.

In another advantageous embodiment of the invention, it is envisaged to use solvents comprising chloroform, methanol, ethanol, amyl acetate, amyl alcohol, cyclohexanone, dimethylsulfoxide, diethylacetamide, dimethylformamide, acetone, acetonitrile, isopropyl acetate, methylene chloride, methyl ketone, methyl isobutyl ketone, cellosolve, tetrahydrofuran, methyl acetate, pyridine, butyl acetate, dioxane, ethyl acetate, dimethylacetamide, trifluoroacetic acid, oxidants, acids, bases, and/or enzymes as solvents, particularly in partial or complete dissolving or removal of the embedding medium or of the first support. Solvents in the meaning of the invention are substances capable of dissolving others biologically, chemically and/or physically, particularly inorganic and organic liquids capable of dissolving other gaseous, liquid or solid substances. For example, inorganic solvents can be classified in solvents containing protons and solvents free of protons, as well as in aqueous and non-aqueous solvents. For example, organic solvents are alcohols such as methanol, ethanol, propanols, butanols, octanols, and cyclohexanol, glycols such as ethylene glycol and diethylglycol, ethers and glycol ethers such as diethyl ether, dibutyl ether, anisole, dioxane, tetrahydrofuran, mono-, di-, tri-, and/or polyethylene glycol ethers, ketones such as acetone, butanone and cyclohexanone, esters such as acetic acid esters and glycol esters, amides and other nitrogen compounds, such as dimethylformamide, pyridine and acetonitrile, sulfur compounds such as carbon disulfide, dimethylsulfoxide and sulfolane, nitro compounds such as nitrobenzene, halohydrocarbons such as dichloromethane, chloroform, tetrachloromethane, tri- and tetrachloroethene, ethylene chloride, and chlorofluorohydrocarbons, hydrocarbons such as gasolines, petroleum ether, cyclohexane, methylcyclohexane, decaline, terpene solvents, benzene, toluene, xylenes, and propylene oxide. However, oxidizing agents can also be used as solvents, e.g. agents which release oxygen to transfer it to other materials, such as potassium permanganate, potassium chlorate and/or lead dioxide, and those having dehydrogenating effect, i.e., withdraw hydrogen from other materials or absorb hydrogen, such as iodine and photooxidants; that is, oxidants according to the invention generally are such elements and compounds having a tendency of forming stable electron shells by electron acceptance to reach a state of lower energy, e.g. sodium ethanolate, sodium metaperiodate, and hydrogen peroxide. Of course, the solvent may also comprise enzymes. Examples of such enzymes are: oxidoreductases, transferases, hydrolases, lyases, isomerases, and/or ligases, proteases, and collagenase. Enzymes in the meaning of the invention are all those proteins, peptides, lipids and/or carbohydrates which, as biocatalysts, are capable of modifying chemical reactions, e.g. cellulase, gelatinase or agarase.

In another advantageous embodiment of the invention, the possible use of a microtome, cryomicrotome, ultramicrotome, ultracryomicrotome, and/or vibratome is envisaged to separate the embedded supports. To produce sections, a microtome is particularly suitable in those cases where paraffin is used as embedding medium. For example, the outstanding feature of a cryomicrotome is that, as a result of treatment at low temperatures of from −10 to −70° C., the samples are treated particularly carefully, and aqueous embedding media can preferably be used with a similar effect of careful treatment. An ultramicrotome is used in those cases where synthetic resins are employed as embedding media and/or particularly thin sections especially with a thickness of from 20 nm to 1 µm are produced. Such thin sections result in a particularly economic use of the materials immobilized on the first support. Obviously, the ultramicrotomy can also be performed as a cryomicrotomy. In particular, a vibratome is used in those cases where the first support to be dissected has a consistency comparable to chemically fixed, biological tissue. In this event, an additional embedding medium to prepare the sections is not required. A vibratome can also be used where the embedding medium has appropriate consistency, e.g. serum albumin crosslinked with glutardialdehyde and/or cured collagen.

In another advantageous embodiment of the invention, it is envisaged that detection molecules immobilized on the first support are crosslinked prior to and/or during and/or subsequent to the removal of the first support by incubation with formaldehyde, glutaraldehyde, glacial acetic acid, bivalent coupling reagents, and/or by polyvalent coupling reagents, particularly oxidized dextran, tosyl-activated dextran, polylysine, activated polylysine, proteins, activated proteins, activated nucleic acids, activated polycarbonates and/or polyethylene glycols. Incubation with these various substances causes crosslinking of the detection molecules in a way to make coating on the second support easy.

One advantage of the method according to the invention is that separating the process of immobilization on the first support from applying the sections on a second support allows more specific and more efficient selection of the supports compared to those cases where the support having the detection molecules immobilized thereon is the same support that is used in detection. In particular, the first support is selected such that a largest possible number of detection molecules can be immobilized e.g. by existing hydrophobic or hydrophilic interactions, by specific functional groups, by epoxy activation, aldehyde activation, by branched linkers, or by electrically charged macromolecular materials coated thereon. In contrast, the second support is designed according to specific aspects of the respective use of the array. For use in clinical diagnostics, for example, glass arrays or test strips made of cellulose have become well-established, but to date, coating and immobilizing detection molecules thereon has not been possible with the required density, reproducibility and efficiency.

Another advantage of the method is that the detection molecules and/or biomolecules coated on the first support can be crosslinked with each other and, following dissolution of the first support, can form a three-dimensional network on the second support which offers optimum access to a component and/or to sample molecules.

Employing two supports allows the use of e.g. a first support with high binding capacity for detection molecules and a second support having good optical properties, i.e., low autofluorescence, for example. By complete or partial dissolution of the first support, it is possible to reduce or avoid interfering optical properties of the first support. At the same time, however, it is possible to ensure high occupation density of detection molecules on the second support, enabling optimum fluorescence detection.

Another advantage of the method according to the invention is that the detection molecules can be immobilized with high-density packing. In particular, the packing density follows from the spot density and/or line density of the detection molecules on a first support and from packing multiple first supports one on top of the other. Using the method of the invention, the arrays can be produced with high reproducibility and at low cost. By transferring the first support on the bottom of a microtest plate, the detection system is brought into an automatizable system environment which is standard in many laboratories and especially in routine laboratories.

Without intending to be limiting, the invention will be explained in more detail with reference to the following examples.

EXAMPLE 1

Transfer of a Western Blot from Nitrocellulose on a Glass Slide and Subsequent Determination of Pathogen-Specific Human IgG Bacterial crude extracts from *Borrelia burgdorferi*, *Chlamydia trachomatis*, *Yersinia enterocolytica*, *Campylobacter jejuni*, *Mycoplasma pneumoniae* and *Salmonella* spec. are adjusted to a protein concentration of 1 mg/ml by diluting with distilled water. Subsequently, 10 µg of each crude extract is separated in a polyacrylamide gel disk electrophoresis (Laemmli, 1970, Nature, 227; 680–685) (10% gel, 1 mm gel thickness, comb 10, electrophoretic chamber: Mini-Protean II, Biorad). Using electroblotting (Towbin et al., 1979, Proc. Natl. Acad. Sci. U.S.A. 76, 4350–4354), the separated proteins are transferred from the gel onto a nitrocellulose membrane (Life Technologies).

The dried lanes of each bacterial crude extract are cut out of the nitrocellulose film and cut into 20 pieces of 0.5 cm. In a well-defined order and one on top of the other, the pieces are placed in a flexible metal frame which has one interruption and is situated in a glass dish with a planar bottom and a diameter of 5 cm. Between the nitrocellulose pieces having blotted proteins thereon, 3 nitrocellulose pieces of identical size are placed as spacers. The glass dish is preheated to 60° C. and filled up with liquid paraffin to a height of 1 cm without changing the order of the nitrocellulose pieces. Care should be taken to remove air bubbles possibly situated between the nitrocellulose pieces by gentle agitation or by applying a vacuum. The dish filled with paraffin is incubated at 60° C. overnight. Thereafter, the dish is rapidly cooled, and the metal frame including the nitrocellulose strips is cut out of the whole block. Ultimately, the block including the nitrocellulose pieces is exposed by bending the metal frame and secured on a microtome in order to prepare the paraffin sections.

Sections 10 µm in thickness are prepared and placed on glass slides, one at a time, which have been treated with proteoglycerol according to standard procedures. Following "stretching" of the paraffin section on a drop of water at 60° C., the water is sucked off, the section is positioned and dried at 37° C. for at least about 2 hours.

Following drying, the sections are made free of paraffin by placing the slides in xylene. Thereafter, the slides are washed twice in 100% ethanol and twice in 100% acetone for 5 minutes each time, subsequently rehydrated in water for 2 minutes each time, and equilibrated in 0.05 M sodium phosphate buffer, pH 7.4,+0.1% Tween, for 15 minutes.

Subsequently, the slides are blocked in 1% human serum albumin in PBS-T for 30 minutes.

Now, the slides are incubated at room temperature for 1 hour with human serums diluted 1:100 in PBS-T. Thereafter, the slides are placed in PBS-T and washed for 30 minutes, changing the washing fluid three times. This is subsequently incubated with ScreenBeads-Rhodamin (Chemicell) having anti-human IgG antiserum (IgG fraction) (Rockland) coupled thereto, at a dilution of 1:1000 in PBS-T for 1 hour at room temperature. Following washing the slides with PBS-T for 30 minutes, changing the washing fluid three times, and brief immersion in distilled water, the slides are dried and evaluated using a laser cryptoscope (IOM). The measured rhodamine fluorescence is proportional to the amount of specifically bound human IgG. Alternatively, a peroxidase can be coupled to the anti-human IgG antiserum (IgG fraction). Following incubation with the antibody-peroxidase conjugate and the subsequent washing step, the slides are incubated with diaminobenzidine substrate solution according to standard procedures. Evaluation in this case is effected using a scanner or a CCD camera.

EXAMPLE 2

Transfer of a Western Blot from Nitrocellulose on a PVDF Membrane and Determination of Pathogen-Specific Human IgG A bacterial crude extract of *Borrelia burgdorferi* is separated in a polyacrylamide gel electrophoresis and blotted on a nitrocellulose membrane as in Example 1. The following specific bands are cut out of the nitrocellulose blotting membrane using a scalpel: 83 kD, 41 kD, 39 kD, 34 kD, 31 kD (Osp A), 28/29 kD (Osp D), 25 kD (Osp C), 21 kD. The bands can be composed from different blots to ensure optimum representation of the respective protein. The cut-out bands are then adhered on a second membrane (nitrocellulose or PVDF) at 2 mm intervals in a well-defined arrangement. The second membrane now is enclosed in a paraffin block and cut into sections 10 µm in thickness along the perpendicular to the length of the protein bands. The sections are stretched at 56° C. on a water surface, transferred onto a PVDF membrane and dried at 45° C. Subsequently, the paraffin is completely removed by incubation with xylene or Rotihistol (Roth). To this end, the PVDF membrane is transferred on a filter paper soaked with the solvent and incubated in a sealed chamber for two hours. Thereafter, the PVDF membrane is incubated twice with 100% methanol in the same way for 5 minutes, subsequently in DMSO for 1 hour, and then in water for one hour.

Thereafter, the PVDF membrane is equilibrated in 0.05 M Tris-HCl buffer, pH 7.4, and 0.1% Tween 20 (TBS-T) and subsequently blocked for one hour by adding 1% human serum albumin.

Subsequently, the membranes thus prepared are incubated for one hour with patient serums previously diluted in TBS-T.

Following several washings in TBS-T, the membranes are incubated with anti-human IgG peroxidase (Rockland) at a dilution of 1:2000 in TBS-T for one hour. Following several washings in TBS-T, the peroxidase-substrate reaction is performed for 15 minutes using TMB ready-to-use solution (Seramun).

All incubations in the immune detection are performed at room temperature.

What is claimed is:

1. A method of producing an array for the detection of components from a biological sample, wherein
   (a) detection molecules are immobilized on one or more first supports using transfer procedures comprising electroblotting said first support comprising a membrane,
   (b) the first support(s) is/are embedded in a material, said material is caused to cure,
   (c) the embedded first support(s) is/are separated into sections, wherein each section comprises detection molecules,
   (d) at least one section of the first support is applied on a second support to form an applied section, and
   (e) removing the cured material and partially dissolving or partially removing said first support from the applied section using a solvent, wherein said removing results in immobilization on said second support of said first support comprising detection molecules, whereby an array is obtained.

2. The method according to claim 1, wherein at least two first supports overlap with each other, and are embedded in the material of step (b).

3. The method according to claim 1, wherein the detection molecules comprise ligands, antigens, antibodies, receptors, nucleic acids, lectins, peptides, glycopeptides, carbohydrates, or lipids.

4. The method according to claim 1, wherein the detection molecules are immobilized on the first support in the form of multiple lines.

5. The method according to claim 1, wherein the detection molecules are transferred from a gel on to the first support by electroblotting.

6. The method according to claim 1, wherein the first support comprises nitrocellulose, cellulose acetate, cellulose mixed esters, polytetrafluoroethylene (PTFE), polyamide, regenerated cellulose, polycarbonate, polyester, polysulfone, polyacrylamide, agarose, nylon, or polyprene.

7. The method according to claim 1, wherein the curing material comprises saturated aliphatic hydrocarbons, especially paraffin, embedding resins, collagen solutions, aqueous solutions, solutions of crosslinking proteins, carbohydrates, nucleic acids, polymers, or agarose.

8. The method according to claim 1, wherein the second support comprises a metal, polypropylene, teflon, polyethylene, polystyrene, ceramics, or glass.

9. The method according to claim 1, wherein the surface of the first support is modified.

10. The method according to claim 1, wherein the solvent comprises solvents comprising chloroform, methanol, ethanol, amyl acetate, amyl alcohol, cyclohexanone, dimethylsulfoxide, diethylacetamide, dimethylformamide, acetone, acetonitrile, isopropyl acetate, methylene chloride, methyl ketone, methyl isobutyl ketone, cellosolve, tetrahydrofuran, methyl acetate, pyridine, butyl acetate, dioxane, ethyl acetate, dimethylacetamide, trifluoroacetic acid, oxidants, acids, bases, enzymes.

11. The method according to claim 1, wherein the embedded supports of step (c) are separated into sections using a microtome, a cryomicrotome, an ultramicrotome, an ultracryomicrotome, or a vibratome.

12. The method according to claim 1, further comprising treating the detection molecules with formaldehyde, glutaraldehyde, glacial acetic acid, bivalent coupling reagents, oxidized dextran, tosyl-activated dextran, polylysine, activated polylysine, activated polycarbonates or polyethylene glycols.

13. The method according to claim 1, wherein the surface of the second support is modified.

14. The method according to claim 1, wherein said removing (e) results in said detection molecules being in contact with the second support.

15. The method according to claim 1, wherein said removing results in said detection molecules being in contact with remaining first support after said removing (e).

16. The method according to claim 1, wherein the detection molecules are separated in a gel by electrophoresis prior to said electroblotting.

17. The method according to claim 16, wherein said removing results in said detection molecules being in contact with remaining first support after said removing (e).

18. A method according to claim 1, wherein the first support is nitrocellulose.

19. The method according to claim 1, wherein the second support is polyvinylidene difluoride (PVDF).

* * * * *